United States Patent [19]

Gaffar et al.

[11] 4,177,258

[45] Dec. 4, 1979

[54] DENTIFRICE FOR DENTAL REMINERALIZATION

[75] Inventors: Maria C. S. Gaffar; Abdul Gaffar, both of Somerset, N.J.

[73] Assignee: Colgate Palmolive Company, New York, N.Y.

[21] Appl. No.: 20,377

[22] Filed: Mar. 14, 1979

Related U.S. Application Data

[63] Continuation-in-part of Ser. No. 951,893, Oct. 13, 1978.

[51] Int. Cl.² .................... A61K 7/18; A61K 7/22
[52] U.S. Cl. ........................ 424/52; 424/49; 424/54; 424/56; 424/57
[58] Field of Search .................... 424/49–58

[56] References Cited

U.S. PATENT DOCUMENTS

| Re. 29,182 | 4/1977 | McCune et al. | 424/49 |
|---|---|---|---|
| 3,288,846 | 11/1966 | Irani et al. | 260/502 P |
| 3,298,956 | 1/1967 | Irani et al. | 260/502 P |
| 3,336,221 | 8/1967 | Ralston | 260/502 P |
| 3,434,969 | 3/1969 | Ralston | 260/502 P |
| 3,625,569 | 2/1972 | Medcalf | 424/48 |
| 3,671,644 | 6/1972 | Irani et al. | 424/329 |
| 3,792,152 | 2/1974 | Kim | 423/311 |
| 3,832,396 | 8/1974 | Irani et al. | 260/502 P |
| 4,097,588 | 6/1978 | Levine | 424/52 |
| 4,110,429 | 8/1978 | Gaffar et al. | 424/49 |

FOREIGN PATENT DOCUMENTS

| 1617729 | 4/1971 | Fed. Rep. of Germany . |
|---|---|---|
| 1515665 | 3/1968 | France . |
| 2159507 | 5/1978 | France . |
| 1344815 | 5/1974 | United Kingdom . |
| 1394034 | 5/1975 | United Kingdom . |

OTHER PUBLICATIONS

Meyer and Nancollas, Calc. Tiss. Res. 13:245–303 (1973), The Influence of Multi-Dentate Phosphonates on the Crystal Growth of Hydroxyapatite.
Briner et al., Calc. Tiss. Res. 7:249–256 (1971), Factors Affecting the Rate of Post-Eruptive Maturation of Dental Enamel.
Monsanto Co. Brochure, "Dequest" Organophosphorus Compounds, Feb. 1971.

Primary Examiner—Shep K. Rose
Attorney, Agent, or Firm—Robert L. Stone; Murray M. Grill; Herbert S. Sylvester

[57] ABSTRACT

A dentifrice useful for remineralizing subsurface carious lesions of dental enamel which contains sources of calcium ions and phosphate ions as well as fluoride ions and further includes as agent to stabilize against precipitation of the calcium and phosphate ions, an antinucleating agent such as ethylenediamine tetramethylenephosphonic acid or water soluble salt thereof, the pH of the dentifrice being about 5–9, preferably close to physiological conditions, such as about 6.8–7.5.

15 Claims, No Drawings

DENTIFRICE FOR DENTAL REMINERALIZATION

This application is a continuation-in-part of application Ser. No. 951,893, filed Oct. 13, 1978.

This invention relates to a dentifrice which is effective to remineralize various lesions in dental enamel.

It is known that dental caries begin with lesions of so-called "white spots," which are demineralized areas below the surface of intact dental enamel. If unchecked, surface enamel above a sub-surface lesion eventually collapses, leading to cavitation and subsequent loss of tooth structure.

In order to arrest demineralization, and, indeed, in order to remineralize "white spots" various compositions have been proposed. For instance, U.S. Pat. No. 3,679,360 to Rubin et al discloses deposition of calcium phosphate from a gel onto a tooth surface. This, however, does not reach the sub-surface area where demineralization initially occurs. Further, because of the difficulty of maintaining both calcium ions and phosphate ions available without precipitating a calcium phosphate material, two part kits have been proposed in which a calcium component and a phosphate component are sequentially applied to the oral cavity as in British Pat. No. 1,408,922 to Raff et al and British Pat. No. 1,452,125 to Grabenstetter et al or mixed together shortly before such application to form a metastable system with temporary stability as in U.S. Pat. No. 4,080,440 to DiGiulio et al and British Pat. No. 1,509,977 to Levine. Another metastable solution has been described in U.S. Pat. No. 4,097,588 to Levine. Even this solution, however, is not substantially permanent and precipitation can occur, particularly when fluoride ions are present.

It is an advantage of this invention that a remineralizing dentifrice is suitably prepared.

Further advantages will be apparent from consideration of the following specification.

In accordance with certain of its aspects, this invention relates to a remineralizing dentifrice comprising an aqueous humectant vehicle having dissolved therein at least 50 ppm of calcium ions and at least 50 ppm of phosphate ions, the ratio of calcium to phosphate ions being from about 0.01 to about 100:1, the amount of calcium ions and phosphate ions being insufficient to precipitate and sufficient to effect remineralization of dental enamel; said dentifrice further comprising a gelling agent, a compound which provides fluoride anticaries agent and an antinucleating agent selected from the group of acids and orally acceptable water-soluble salts thereof consisting of: diamine tetramethylenephosphonic acids of the formula $(M_2O_3PH_2C)_2N(CH_2PO_3M_2)_2$ wherein n is an integer from 1 to 10; phosphonoacetic acid or salt thereof of the formula $M_2O_3PCH_2COOM$; peroxydiphosphate of the formula $M_4P_2O_8$; an oligomer

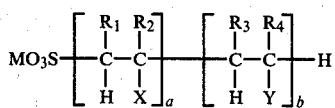

in which M is hydrogen or an orally acceptable cation; $R_1$, $R_2$, $R_3$, and $R_4$ are independently hydrogen, methyl or ethyl; Y is at least one hydrophilic member of the group consisting of COOM, $-CONH_2$ and $CH_2OH$; X is at least one hydrophobic member of the group consisting of $-CN$, $-COOR$, $-COOR_5OR$, $-CONHR$ and $COONHR_5COR$; R is $C_{1-8}$ alkyl; $R_5$ is $C_{1-4}$ alkylene a is 0–7 and a+b is about 4–15; said dentifrice having a pH of about 5 to about 9.

The antinucleating properties of the agents employed in the present invention appear to be effective to prevent precipitate formation from the calcium and phosphate ions in the dentifrice particularly with the fluoride ions also present. As described in Ciba Foundation Symposium, "Hard Tissue Growth Repair and Remineralization (Elsevier)," Associated Scientific Publishers, New York, 1973 in the article by Francis et al, "Chemical Agents in the Control of Calcification Processes in Biological Systems," pages 57–83, particularly at pages 75–78, an antinucleating agent (e.g., a diphosphonate) can in sufficient quantity at a physiological pH completely absorb onto a spherical nucleated particle of hydroxyapatite as it forms and entirely block crystal growth. In this way, the formation of large insoluble crystals of apatite is prevented and coated small hydroxyapatite crystals of higher water solubility are attained.

It has been found that not all antinucleating agents can successfully stabilize calcium ions and phosphate ions against precipitating to form large insoluble apatite crystals. For instance, such insoluble crystals from which it is sought to use antinucleating agents such as sodium hexametaphosphate, sodium pyrophosphate, sodium phytate and mellitic acid as well as disodium phosphonoethane-1,2-dicarboxylate, 1,1-diphosphonopropane-2,3-dicarboxylic acid monohydrate, 3-amino-1-hydroxypropane-1,1-diphosphonic acid and imino-diacetic-N-methylene phosphonic acid. On the other hand, the antinucleating agents of the present invention successfully stabilize the calcium ions and phosphate ions against precipitation as large insoluble apatite crystals at a pH between about 5 and about 9. Preferably, the pH is about 6.8 to about 7.5, which approximates usual human physiological conditions and is optimum for effecting remineralization. Desirably, the antinucleating agent of the invention is present in amount of about 10 to 5000 ppm ($1 \times 10^{-5}$ M to $1 \times 10^{-2}$ M) of the dentifrice, preferably about 250 to 2500 ppm ($5 \times 10^{-5}$ M to $5 \times 10^{-2}$ M), such as about 2250 ppm ($5 \times 10^{-3}$ M).

The antinucleating agent of the invention is desirably a diamine tetramethylenephosphonic acid of the formula $(M_2O_3PH_2C)_2-N(CH_2)_n-(CH_2PO_3M_2)_2$ wherein n is an integer from 1 to 10 and M is hydrogen or an orally acceptable cation such as alkali metal (e.g. sodium or potassium), ammonium or $C_1-C_{18}$ mono-, di- or trisubstituted ammonium (e.g. mono-, di- or triethanolammonium) salt.

The polyamine polyphosphonic compounds which are most preferred are ethylenediamine tetra (methylenephosphonic acid), (hereinafter EDITEMPA) and its water-soluble orally acceptable salts, (e.g., sodium, potassium, and ammonium and other pharmaceutically acceptable salts; most preferably the tri-, tetra- or penta-sodium salts), other polyamine polyphosphonic compounds include: tetramethylenediamine tetra (methylenephosphonic acid), pentamethylene diamine tetra 8methylenephosphonic acid), hexamethylenediamine tetra (methylelephosphonic acid) and the water-soluble salts of these acids, e.g., sodium, potassium, ammonium and other orally acceptable salts.

Phosphonoacetic acid (hereinafter PAA) and its water soluble orally acceptable salts are also desirable antinucleating agents. They are characterized by the formula $M_2O_3PCH_2COOM$, wherein M has the meaning indicated above.

The peroxydiphosphate (hereinafter PODP) and particularly the alkali metal salts thereof (e.g. potassium or sodium) are likewise desirable antinucleating agents. They are characterized by the formula $M_4P_2O_8$ wherein M has the meaning indicated above.

The desirable oligomer antinucleating agents and methods for their preparation are described in U.S. Pat. Nos. 3,646,099 and 3,859,260, the disclosures of which are incorporated herein by reference. They have the formula:

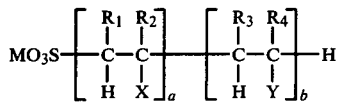

wherein

M is hydrogen or a water soluble orally acceptable cation (as indicated above):

$R_1$, $R_2$, $R_3$ and $R_4$ are independently H, methyl or ethyl;

Y is at least one hydrophilic member of the group consisting of —COOM, —COHN$_2$ and —CH$_2$OH;

X is at least one hydrophobic member of the group consisting of —CN, —COOR, —COOR$_5$OR, —CONHR and —COONHR$_5$COR, R is $C_{1-8}$ alkyl;

$R_5$ is $C_{1-4}$ alkylene;

a is 0–7; and a+b is about 4–15.

These oligomers are anionic and of relatively low and accurately regulated degree of polymerization, (in contrast to the conventional free radical redox polymerization conducted with an oxidative initiator such as hydrogen, alkyl, or acyl peroxides, persulfates or hydroperoxides in relatively large amounts and a reductive activator such as $NaHSO_3$, $Na_2S_2O_4$ or sodium formaldehyde sulfoxylate in relatively low amounts generally added subsequently to the polymerization medium) are prepared by a reductive polymerization in which a much larger amount of a bisulfite salt, e.g. $NaHSO_3$ (sodium bisulfite, sodium acid sulfite), a reducing agent, is the initiator charged initially with the monomer, and an oxidizing agent is added in smaller amounts as the activator during the polymerizing or oligomerizing process.

Subscript a in the formula represents the number of moles of hydrophobic groups, and subscript b the number of moles of hydrophilic groups, in the oligomer molecule. The proportion of X (i.e. the value of a) must be small enough, or even zero, to avoid the production of a too large, sticky and hydrophobic polymer molecule, and will of course be dependent for the most part in any particular instance on the identity of the X and Y groups, i.e. the hydrophobic-containing and hydrophilic containing monomeric reactants. Mixtures of such oligomers may of course also be employed.

Examples of monomers containing hydrophilic Y group are acrylic acid, methacrylic acid, alpha-ethylacrylic acid, beta-methylacrylic acid, alpha, beta-dimethylacrylic acid, orally acceptable salts of these acids, for example those containing such cations as alkali metal (e.g. sodium and potassium), ammonium, $C_{1-18}$ mono-, di- and tri-substituted ammonium (e.g. alkanol substituted such as mono-, di- and tri-ethanolammonium), etc., acrylamide, methacrylamide, ethacrylamide, and allyl alcohol and the like.

Examples of monomers containing hydrophobic X groups are acrylonitrile, methacrylonitrile, ethacrylonitrile, methyl and ethyl and octyl acrylate and methacrylate, methoxyethyl acrylate, octoxyethyl methacrylate, ethoxybutyl methacrylate, propoxymethyl acrylate, N-ethylacrylamide, N-isopropylacrylamide, N-methylacrylamide, N-propylethacrylamide, vinyl acetate, propionate and octanoate, diacetone acrylamide and the like.

The oligomerization is carried out in water in the presence of a relatively large amount of the bisulfite reducing initiator, expressed in mols of monomer/gram formula weight (gFW) of reducing initiator is about 4 to 15, this ratio determining the degree of oligomerization.

The reductive initiator is preferably a water soluble bisulfite salt (M in the formula), especially alkali metal, such as sodium or potassium, but bisulfite salts containing other orally acceptable cations of the type referred to above may be employed.

In practice, enough oxidative activator is used to effect 100% conversion of the monomers to oligomers. The amount of such activator, expressed as gFW activator/gFw initiator may range from 0.0001 to 0.1 but usually is from about 0.0001 to 0.1. Examples of these oxidative activators are ammonium, sodium potassium persulfate, hydrogen peroxide and other water soluble oxidants commonly employed in the polymerization art.

Following completion of the oligomerization reaction, any free carboxylic acids groups in the oligomer molecules may, if desired be partially or completely neutralized, preferably at least 60%, by treating the aqueous oligomer solution with a suitable base to convert such groups to their salts with orally acceptable cations as referred to above. These aqueous oligomer solutions have a highly desirable low viscosity, and low molecular weight range depending on the monomer units in the oligomer.

It will be understood that the oligomer formula above is not intended to depict the actual structure of the oligomer molecule, the bracketed units of which formula are randomly distributed in the molecule with the —SO$_3$M group being normally bonded to a terminal carbon atom in the oligomer chain devoid of X and or Y substituents. In the oligomers preferred for use herein, a is zero, Y is —COOM, $R_1$–$R_4$ are H, and M is alkali metal, e.g. sodium, b being about 10, as derived from acrylic acid. An oligomer of the formula above in the form of its sodium salt, with a molecular weight of about 1,000, containing about 10 acrylic acid monomeric units, is commercially available under the trade name ND-2 (a product of UniRoyal).

The effective antinucleating agents render the remineralizing dentifrice stable at normally occurring temperatures, e.g., about 15° C.–40° C. The remineralizing agents can diffuse effectively through an intact enamel surface in order to act on subsurface lesions.

The stability provided by the effective antinucleating agents prevents spontaneous precipitation on enamel surfaces and thereby permits diffusion of the remineralizing components to subsurface lesions.

One or more sources of each calcium ions and phosphate ions may be employed. When the source is normally insoluble such as a calcium phosphate, it is solubilized during preparation of the solution, by maintaining an acid pH of about 6 or less (e.g., about 2.5 to 6) during preparation of the remineralizing solution, particularly before the effective antinucleating agent is added.

The normally insoluble sources of calcium and phosphate ions may be a single compound such as tricalcium phosphate (which substantially corresponds to hydroxyapatite, $Ca_5(PO_4)_3OH$ or $3Ca_3(PO_4)_2 \cdot Ca(OH)_2$, bone meal or dicalcium phosphate (dihydrate or anhydrous). When dissolved, particularly in the presence of fluoride ions, formation of hydroxyapatite, fluorohydroxyapatite and fluorapatite occurs.

Examples of other normally water-soluble or normally water-insoluble (but soluble at pH of about 6 or less) sources of calcium ion, but not phosphate ion, which can be used in the remineralizing dentifrice of the invention include calcium salts with acetate, gluconate, nitrate, stearate, lactate, formate, molybdate, tungstate, sulfate, alkyl sulfonate (e.g. lauryl sulfonate), oleate, tartrate, sorbate, iodate, silicate, aluminate, benzoate, citrate, fumarate, butyrate, isobutyrate, malate, maleate, propionate, valerate and the like. Mixtures of such calcium sources with each other or with calcium phosphate may be employed.

Examples of sources of phosphate ions, but not calcium ion, which can be used in the remineralizing dentifrice of the invention include the normally water-soluble or normally water-insoluble (but soluble at pH of about 6 or less) salts including alkali metal (e.g. sodium and potassium), ammonium, magnesium, barium and strontium orthophosphates and acid orthophosphates, metaphosphates, pyrophosphates, as well as glycerophosphates, fructose-6-phosphate, sorbitol-6-phosphate, glucose-1-phosphate, glucose-6-phosphate and the like. Mixtures of such phosphate sources with each other or with calcium phosphate may be employed.

Tricalcium phosphate or the other sources of calcium and phosphate which together form hydroxyapatite when dissolved are employed with the mole ratio of calcium ion to phosphate ion being from about 0.01 to about 100:1, typically about 0.2 to about 5:1, preferably about 1.2 to about 2:1, e.g., about 1.4 to about 1.7:1. A ratio of calcium to phosphate of 1.67:1 corresponds to the ratio of calcium to phosphate in dental enamel. The amount of calcium ion and phosphate ion in the dentifrice is sufficient to effect remineralization, there being typically at least about 500 ppm of each of calcium ion and phosphate ion. The maximum amount of calcium ion and phosphate ion desirable is that which would not result in precipitate formation. This could vary depending on the ion sources and the pH conditions. Typically, about 35,000 ppm of calcium ion and about 40,000 ppm of phosphate can be employed and precipitation still avoided.

In the prior art it has been difficult to maintain the solubility of calcium phosphate, particularly in the presence of a fluoride source. As previously indicated, this is overcome in the present invention when the effective antinucleating agents are employed. Examples of fluoride ion sources (including complex fluoride ions) include alkali metal (e.g., sodium potassium and lithium) ammonium, alkaline earth metal (e.g., calcium, barium, strontium, magnesium), aluminum, zinc, stannous, indium, zirconium, copper, nickel, palladium and organonitrogen such as alkylamine (e.g., hexylamine) compounds with fluoride ion sources. Sources of fluoride ions include fluoride, fluorophosphate (including monofluorophosphate, difluorophosphate and polyfluorophosphate), silicofluoride, fluorozirconate, fluoroborate and fluorostannite. Typical compounds are sodium fluoride, zinc fluoride, stannous fluoride and sodium monofluorophosphate. Sodium fluoride and sodium monofluorophosphate are preferred. The fluoride source compound is desirably present in amount to provide about 1 ppm to 10,000 ppm(0.0001%-1%)fluoride to the remineralizing dentifrice e.g., about 1 ppm to 1000 ppm (0.0001-0.76%)sodium monofluorophosphate, preferably about 5 ppm fluoride. The amount of the compound employed should not be sufficient to result in precipitate formation. For instance, in the case of a fluoride source of low solubility, such as calcium fluoride, the amount of the compound employed should not exceed 1500 ppm.

The stable remineralizing dentifrice may be made by first preparing a stock solution of soluble calcium ions from a solution of a water-soluble salt such as calcium chloride and phosphate ions from a solution of a water salt such as sodium dihydrogen phosphate; one or both of the calcium or phosphate solutions preferably containing antinucleating agent such as EDITEMPA, prior to forming the stock solution in order to prevent spontaneous precipitation. A preferred final concentration of calcium ions and phosphate ions in the stock solution is about 1.5 mM and 0.9 mM respectively. A water-soluble salt such as sodium fluoride, stannous fluoride or sodium monofluorophosphate is then added to the stock solution and the pH adjusted, typically to about 5 to 9, typically about 6 to 7, for instance with sodium hydroxide.

The stock solution is then mixed into a dentifrice containing an aqueous humectant vehicle and a gelling agent typically in about equal amounts in order to dissolve the calcium and phosphate ions in the dentifrice.

Alternatively, an insoluble calcium phosphate source such as hydroxyapatite or dicalcium phosphate can be solubilized in clear solution by reducing the pH to about 2-4, typically about 2.8-3.8 with acids such as phosphoric acid, hydrochloric acid and the like. After the antinucleating agent and fluoride are added and the pH raised typically to about 6 to 7, the thus formed solution is mixed into a dentifrice containing an aqueous humectant vehicle in typically about equal amounts, thereby dissolving calcium and phosphate ions therein.

The dentifrice can be maintained for a long period of time, remaining effective when brought into contact with dental material to remineralize sub-surface lesions.

The dentifrice typically contains about 10–50% of a dentally acceptable water-insoluble polishing material. Preferably the polishing material does not include calcium and phosphate moieties. Insoluble polishing materials containing calcium and phosphate moieties, such as dicalcium phosphate, would not provide calcium ions and phosphate ions in the amounts provided by the solubilized material in the dentifrice of the invention. Desirable polishing agents include hydrated alumina, silica (colloidal, precipitated or crystalline), dolomite, bentonite, melamineformaldehyde resin, urea formaldehyde resin and the like. Hydrated alumina and silica are preferred. The dental cream also generally contains humectant such as glycerine, sorbitol, propylene glycol or polyethylene glycol 400 and gelling agent such as sodium carboxymethyl cellulose or Irish Moss. Also, surface active agent flavoring and/or sweetening material, antibacterial agent, antibacterial preservative, (e.g. sodium benzoate or methyl-4-hydroxy benzote), silicone material, chlorophyll compound or ammoniated material may be present.

The following examples illustrate the invention but do not limit it. All parts, amounts and proportions are by weight unless otherwise noted.

EXAMPLE 1

A stock solution of hydroxyapatite (tricalcium phosphate) is prepared by adding a solution containing calcium chloride to a solution of sodium dihydrogen phosphate to a final concentration of 1.5 mM calcium ions and 0.9 mM phosphate ions; the sodium dihydrogen phosphate solution containing EDITEMPA to provide the stock solution with $1 \times 10^{-5}$ M thereof and phosphoric acid to provide the stock solution with a pH of about 3.

The pH is raised to 7 with 1 N potassium hydroxide. Sodium monofluorophosphate is then added to a concentration of 5 ppm fluoride in the stock solution following which sodium chloride is added to give an electrolyte concentration of 50 mM and additional water is added to 1 liter.

The solution thus formed is added in 1:1 ratio to the following dental cream formulation:

|  | PARTS |
| --- | --- |
| Glycerine | 10.00 |
| Sorbitol (70%) | 17.00 |
| Water | 23.70 |
| Sodium Benzoate | 0.50 |
| Sodium Saccharin | 0.20 |
| Sodium Carboxymethyl Cellulose | 1.10 |
| Precipitated Silica | 45.00 |
| Sodium Lauryl Sulfate | 1.50 |
| Flavor | 1.00 |

The dental cream remains stable upon storage and the calcium ions and phosphate ions remain dissolved therein.

EXAMPLE 2

Similar dental creams to that of Example 1 are prepared in which the solution containing calcium ions and phosphate ions contains each of PAA (concentration $5 \times 10^{-3}$M); PODP (concentration $5 \times 10^{-4}$); and Uni-Royal Oligomer ND-2 (concentration $5 \times 10^{-4}$M). The dental creams are stable upon storage and the calcium ions and phosphate ions remain dissolved therein.

EXAMPLE 3

A stock solution of hydroxyapatite (tricalcium phosphate) is prepared by adding hydroxyapatite to water to a final concentration of 1.5 mM calcium ions and 0.9 mM phosphate ions. 0.25 grams of sodium benzoate (from 0.05% solution thereof) are then added to the solution to minimize bacterial growth.

Phosphoric acid is then added to 500 ml of the stock solution to produce a clear solution at pH 3, after which the pH is raised to 6 with 1 N potassium hydroxide. Next EDITEMPA is added and mixed into the solution to a concentration of $1 \times 10^{-5}$ M thereof, following which additional potassium hydroxide is added to produce a pH of 7. Sodium monofluorophosphate is then added to a concentration of 5 ppm fluoride in the stock solution following which sodium chloride is added to give an electrolyte concentration of 50 mM and additional water is added to 1 liter.

The solution thus formed is added in 1:1 ratio to the dental cream formulation set forth in Example 1. The dental cream remains stable upon storage and the calcium ions and phosphate ions remain dissolved therein.

EXAMPLE 4

A similar dental cream to that of Example 3 is prepared in which dicalcium phosphate dihydrate is solubilized in the stock solution in place of hydroxyapatite to give a concentration of 60 ppm of calcium ions and 400 ppm of phosphate ions in the stock solution. The dental cream remains stable upon storage and the calcium ions and phosphate ions remain dissolved therein.

It will be apparent to one skilled in the art that various modifications of the foregoing Examples may be made thereto.

We claim:

1. A remineralizing dentifrice comprising an aqueous humectant vehicle having dissolved therein at least 50 ppm of calcium ions and at least 50 ppm of a source of phosphate ions, the ratio of calcium to phosphate ions being from about 0.01 to about 100:1, the amount of calcium ions and phosphate ions being insufficient to precipitate and sufficient to effect remineralization of dental enamel; said dentifrice further comprising a gelling agent, a compound which provides fluoride anti-caries agent and an antinucleating agent selected from the group of acids and orally acceptable water-soluble salts thereof consisting of: diamine tetramethylenephosphonic acids of the formula $(M_2O_3PH_2C)_2N(CH_2)_nN(CH_2PO_3M_2)_2$, wherein n is an integer from 1 to 10; phosphonoacetic acid or salt thereof of the formula $M_2O_3PCH_2COOM$; peroxydiphosphate of the formula $M_4P_2O_8$; an oligomer

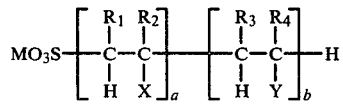

in which M is hydrogen or an orally acceptable cation; $R_1$, $R_2$, $R_3$, and $R_4$ are independently hydrogen, methyl or ethyl; Y is at least one hydrophilic member of the group consisting of —COOM, —CONH$_2$ and CH$_2$OH; X is at least one hydrophobic member of the group consisting of —CN, —COOR, —COOR$_5$OR, —CONHR and —COONHR$_5$COR: R is C$_{1-8}$ alkyl; R$_5$ is C$_{1-4}$ alkylene; a is 0–7 and a+b is about 4–15; said dentifrice having a pH of about 5 to 9.

2. The remineralizing dentifrice claimed in claim 1 wherein said antinucleating agent is present in amount of about 10 to 5000 ppm.

3. The remineralizing dentifrice claimed in claim 1 wherein said antinucleating agent is said diamine tetramethylenephosphonic acid or orally acceptable salt thereof.

4. The remineralizing dentifrice claimed in claim 3 wherein said antinucleating agent is ethylene diamine tetramethylenephosphonic acid or orally acceptable salt thereof.

5. The remineralizing dentifrice claimed in claim 1 wherein said antinucleating agent is said phosphonoacetic acid or orally acceptable salt thereof.

6. The remineralizing dentifrice claimed in claim 1 wherein said antinucleating agent is said orally acceptable peroxydiphosphate.

7. The remineralizing dentifrice claimed in claim 1 wherein said antinucleating agent is said oligomer or orally acceptable salt thereof.

8. The remineralizing dentifrice claimed in claim 1 wherein the mole ratio of calcium to phosphate is from about 0.01 to about 100:1 and at least about 50 ppm of each of calcium and phosphate is present.

9. The remineralizing dentifrice claimed in claim 8 wherein said source of calcium and ions and of phosphate ions is hydroxyapatite and the mole ratio of calcium to phosphate is about 1.67 to 1.

10. The remineralizing dentifrice claimed in claim 1 wherein said source of calcium ions and of phosphate ions is dicalcium phosphate.

11. The remineralizing dentifrice claimed in claim 1 wherein said source of calcium ions is calcium chloride and said source of phosphate ions is sodium dihydrogen phosphate.

12. The remineralizing dentifrice claimed in claim 1 wherein said compound which provides fluoride anticaries agent provides about 1 ppm to about 1000 ppm.

13. The remineralizing dentifrice claimed in claim 12 wherein said compound which provides fluoride anticaries agent is sodium monofluorophosphate.

14. The remineralizing dentifrice claimed in claim 1 wherein said dentifrice is a dental cream and comprises a dentally acceptable water-insoluble polishing material selected from the group consisting of hydrated alumina and silica.

15. The process of preparing a remineralizing dentifrice comprising incorporating into a stock solution containing calcium ions and phosphate ions at a pH of about 2–4 an antinucleating agent which prevents precipitation of said calcium ions and said phosphate ions selected from the group consisting of orally acceptable water-soluble salts thereof consisting of: diamine tetramethylenephosphonic acids of the formula $(M_2O_3PH_2C)_2N(CH_2)_n N(CH_2PO_3M_2)_2$, wherein n is an integer from 1 to 10; phosphonoacetic acid or salt thereof of the formula $M_2O_3PCH_2COOM$; peroxydiphosphate of the formula $M_4P_2O_8$; an oligomer

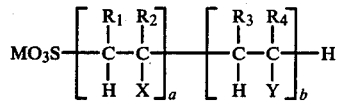

in which M is hydrogen or an orally acceptable cation; $R_1$, $R_2$, $R_3$, and $R_4$ are independently hydrogen, methyl or ethyl; Y is at least one hydrophilic member of the group consisting of —COOM, —CONH$_2$ and CH$_2$OH; X is at least one hydrophobic member of the group consisting of —CN, —COOR, —COOR$_5$OR, —CONHR and —COONHR$_5$COR: R is $C_{1-8}$ alkyl; $R_5$ is $C_{1-4}$ alkylene; a is 0–7 and a+b is about 4–15; adding to said stock solution a compound which provides fluoride anticaries agent, raising the pH to about 5–9 and incorporating said stock solution into a dentifrice comprising an aqueous humectant vehicle and a gelling agent, thereby forming a stable remineralizing dentifrice, said dentifrice having a pH of about 5–9.

* * * * *